United States Patent [19]

Gogins

[11] Patent Number: 4,779,448
[45] Date of Patent: Oct. 25, 1988

[54] PHOTOELECTRIC BUBBLE DETECTOR APPARATUS AND METHOD

[75] Inventor: Mark A. Gogins, Roseville, Minn.

[73] Assignee: Donaldson Company, Inc., Minneapolis, Minn.

[21] Appl. No.: 823,306

[22] Filed: Jan. 28, 1986

[51] Int. Cl.$^4$ ............................................. G01N 15/08
[52] U.S. Cl. .......................................... 73/38; 73/293; 250/574; 364/550
[58] Field of Search ............................ 73/38, 293, 290; 250/221.1, 221.2, 573, 574; 364/550

[56] References Cited

U.S. PATENT DOCUMENTS

| | | |
|---|---|---|
| 2,503,770 | 4/1950 | Robinson . |
| 2,873,644 | 2/1959 | Kremen et al. . |
| 3,007,334 | 11/1961 | Pall .......................... 73/38 |
| 3,446,558 | 5/1969 | Seaton . |
| 3,457,419 | 7/1969 | Rosa . |
| 3,864,044 | 2/1975 | Lyshkow . |
| 3,953,126 | 4/1976 | Kim et al. . |
| 4,247,784 | 1/1981 | Henry ........................ 73/293 |

FOREIGN PATENT DOCUMENTS

| | | | |
|---|---|---|---|
| 3306647 | 8/1984 | Fed. Rep. of Germany | 73/38 |
| 3312729 | 10/1984 | Fed. Rep. of Germany | 73/38 |
| 1078284 | 3/1984 | U.S.S.R. | 73/38 |
| 2140163 | 11/1984 | United Kingdom | 73/38 |

Primary Examiner—Thomas H. Tarcza
Assistant Examiner—David Cain
Attorney, Agent, or Firm—Merchant, Gould, Smith, Edell, Welter & Schmidt

[57] ABSTRACT

A photoelectric buffle detector apparatus (20) including a container (22) containing a liquid (24) having a top surface with a top side and an under side. A light emitting source (60) is positioned for emitting light toward the top surface (42) of the liquid (24). A light detecting source (70) positioned for detecting light emitted from the light emitting source (60) and reflected from the top surface (42) of the liquid (24). The light detecting source (70) outputs a signal indicating the presence of a wave pattern at the top surface (42) of the liquid (24) caused by gas bubbles rising to the top surface (42) of the liquid (24).

8 Claims, 3 Drawing Sheets

PHOTOELECTRIC BUBBLE DETECTOR APPARATUS AND METHOD

BACKGROUND OF THE INVENTION

The present invention relates to a photoelectric bubble detector apparatus and method for detecting bubbles in a liquid medium. More particularly, the present invention relates to a photoelectric bubble detector apparatus for determining the pore size distribution of filter media.

A common filter media test is measuring the maximum pore size of the filter media by clamping a sample of the filter media in a fixture, covering it with a liquid and then raising the air pressure below the filter media until a stream of small bubbles appears from the largest of the filter media pores. Based on the known air pressure and fluid properties, the largest pore size of the filter media can then be calculated. This test is done with a technician watching for the appearance of the bubbles. The test is rather tedious and boring for the technician, as well as rather expensive due to the amount of time involved.

The present invention automates the abovedescribed test procedure and also provides a photoelectric detector apparatus for sensing bubbles in other liquids produced by many different phenomena.

SUMMARY OF THE INVENTION

The present invention relates to a photoelectric bubble detector apparatus including container means for containing a liquid, the liquid having a top surface with a top side and an under side. Light emitting means are present for emitting light toward the surface of the liquid. A disturbance means causes bubbles of gas to rise to the top surface of the liquid from a location below the top surface of the liquid such that waves are generated at the top surface of the liquid. The disturbance means thus causes a moving wave pattern at the top surface of the liquid having a frequency and wavelength determined by the density and surface tension of the liquid. Light detecting means is present for detecting light emitted from the light emitting means and reflected from the top surface of the liquid at an intensity which varies at the frequency of the wave pattern. The light detecting means includes output means for output of a signal indicating the presence of the wave pattern due to the gas bubbles rising to the top surface of the liquid.

The present invention includes two embodiments for the light emitting means and light detecting means. In one embodiment, the light emitting means is located at or below the level of the liquid surface. The light emitting means emits light toward the underside of the liquid surface at an angle less than the critical angle of internal reflection of the liquid surface, so that the emitted light is reflected back below the liquid surface upon reaching that surface. The light detecting means is also located below the level of the liquid surface to receive the reflected light. This embodiment is preferred for use with translucent liquids.

In a second embodiment, the light emitting means and light detecting means are both located above the level of the liquid surface. Light is directed at the top of the liquid surface at an angle less than the critical angle of external reflection of the liquid surface, so that the emitted light is reflected upward from the liquid surface to a light detecting means. This embodiment is preferred for use with opaque liquids.

The present invention further relates to a photoelectric bubbles detector apparatus for determining the pore size distribution of a filter media wherein a disturbance means includes gas means for delivering gas under pressure into the liquid of the container means at a location below the top surface of the liquid. The gas means includes means for providing a path for the flow of the gas into the liquid and further includes means for selectively varying the gas pressure. Fixture means is provided for mounting the filter media in the path of the gas, the filter media prohibiting the flow of the gas into the liquid over a range of gas pressures, such that the wave pattern is not present when the flow of gas is so prohibited. The filter media has a first side facing the liquid and a second side facing the gas under pressure.

The present invention further relates to a method for determining the porosity of a porous filter media, comprising the steps of:

(a) positioning the filter media in association with a reservoir containing a liquid such that the filter media is positioned over an outlet from a source of gas under pressure so that one side of the filter media faces the liquid and the other side faces the gas under pressure;

(b) selectively varying the amount of pressure exerted by the gas against the filter media such that bubbles are formed on the liquid side of the filter media and rise to a top surface of the liquid thereby causing a wave pattern having an associated frequency;

(c) directing light from a light source to the surface of the liquid;

(d) detecting the light directed from the light source and reflected from the top surface of the liquid; and (e) determining the frequency of the wave pattern by determining the frequency of variations in light reflected from the top surface of the liquid.

In one embodiment of the present invention light is reflected off the under side of the top surface of the liquid and detected with a small active area photodetector. The capillary waves created by the emerging bubbles at the surface create a time dependent light level on the photodetector. The signal from the photodetector is then filtered to selectively sense the frequency corresponding to the bubble produced waves.

In one particular embodiment of the present invention, the light source is a 200 milliwatt prefocused incandescent lamp, the detector being a one square millimeter active area phototransistor with the emitter base junction used as a photodiode. The signal is amplified by an op-amp, passively high pass filtered, actively two pole high pass filtered, and then passed to an adjustable threshold comparator with a TTL compatible output. Multiple output pulses are received for each bubble breaking the top surface.

In one embodiment of the present invention, the liquid is isopropanol and the gas under pressure is air under pressure.

In another embodiment of the present invention, an inverted open-ended conical structure is employed to avoid distortion caused by bubbles produced by imperfect sample edge seals. The conical structure diverts the edge bubbles away from the area of the liquid surface which is sensed by the bubble detector. The conical structure allows bubbles from the interior of the sample to reach the liquid surface within the detected area.

The present invention provides several advantages. Because the waves spread out across the surface of the liquid, the reflected signal is very strong and insensitive to the filter media pore positions. The selective filtering also rejects the signal from light reflected by stationary objects such as the fixture or container, and lessens interference from room light. Reflecting light from the under side of the surface instead of the top side of the surface also lessens sensitivity to room light. Signals from waves due to small motions of the fixture or container are at a lower frequency than the bubble generated signals and hence are easily discriminated and can be rejected. For example, the bubble signal frequency is isopropanol is roughly 150 Hz., whereas the fixture motion signal frequency is roughly 20 Hz. As a result, the bubble detector apparatus of the present invention can operate for extended periods of time without false triggering and provides for reliable detection of a single bubble.

The present invention is particularly advantageous in that it discriminates from reflections due to the fixture wherein the filter media is mounted, provides a sufficiently strong signal to enable detection, and is not sensitive to the position of the filter media pores.

Although throughout the specification the present invention is described in terms of an apparatus and method for determining the pore size distribution of a filter media and in particular, the maximum pore size of a filter media, it will be appreciated that the present invention has application to sensing bubbles in other liquids produced by many different phenomena.

These and various other advantages and features of novelty which characterize the invention are features of novelty which characterize the invention are pointed out with particularly in the claims annexed hereto and forming a part thereof. However, for a better understanding of the invention, its advantages and objects attained by its use, reference should be had to the drawings which form a further part hereof and to the accompanying descriptive matter, in which there is illustrated and described a preferred embodiment of the invention.

BRIEF DESCRIPTION OF THE DRAWINGS

In the drawings, in which like reference numerals and letters indicate corresponding parts throughout the several views.

DETAILED DESCRIPTION OF A PREFERRED EMBODIMENT

Figure 2:
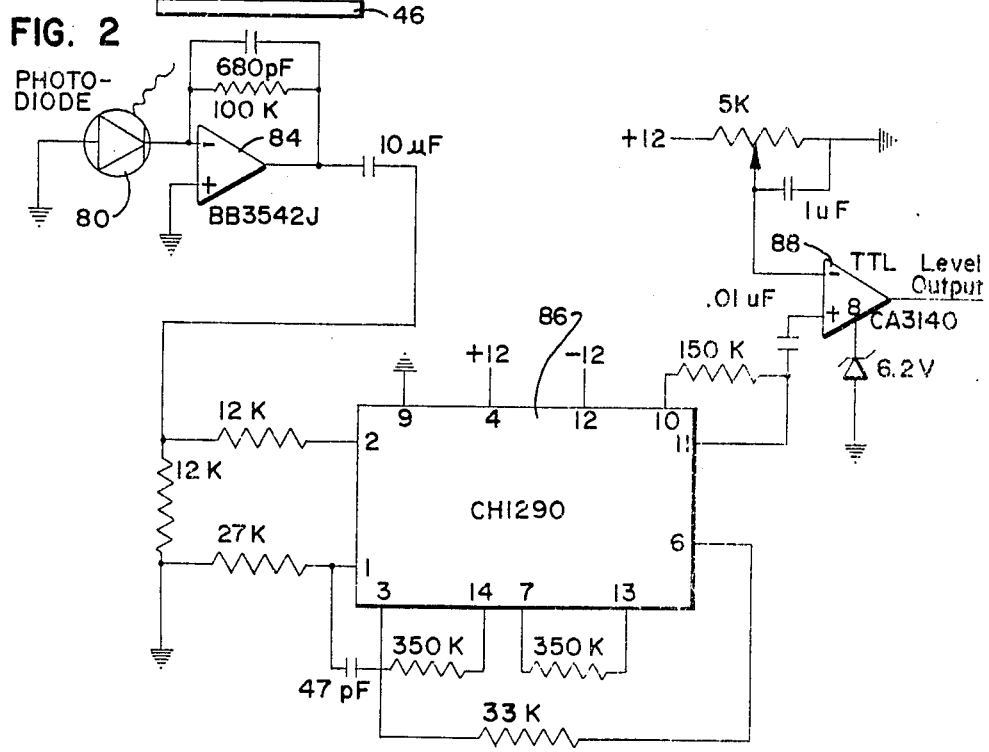
FIG. 2 is a schematic diagram of an embodiment of amplifier, filter and comparator circuitry in accordance with the principles of the present invention.
Figure 3:
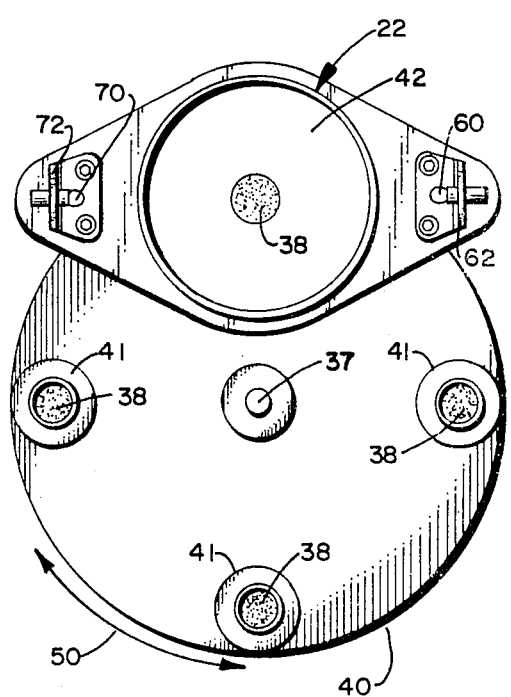
FIG. 3 is a top plan view of an embodiment of a fixture for mounting the filter media in accordance with the principles of the present invention, various components being removed for purposes of illustration.
Figure 4:
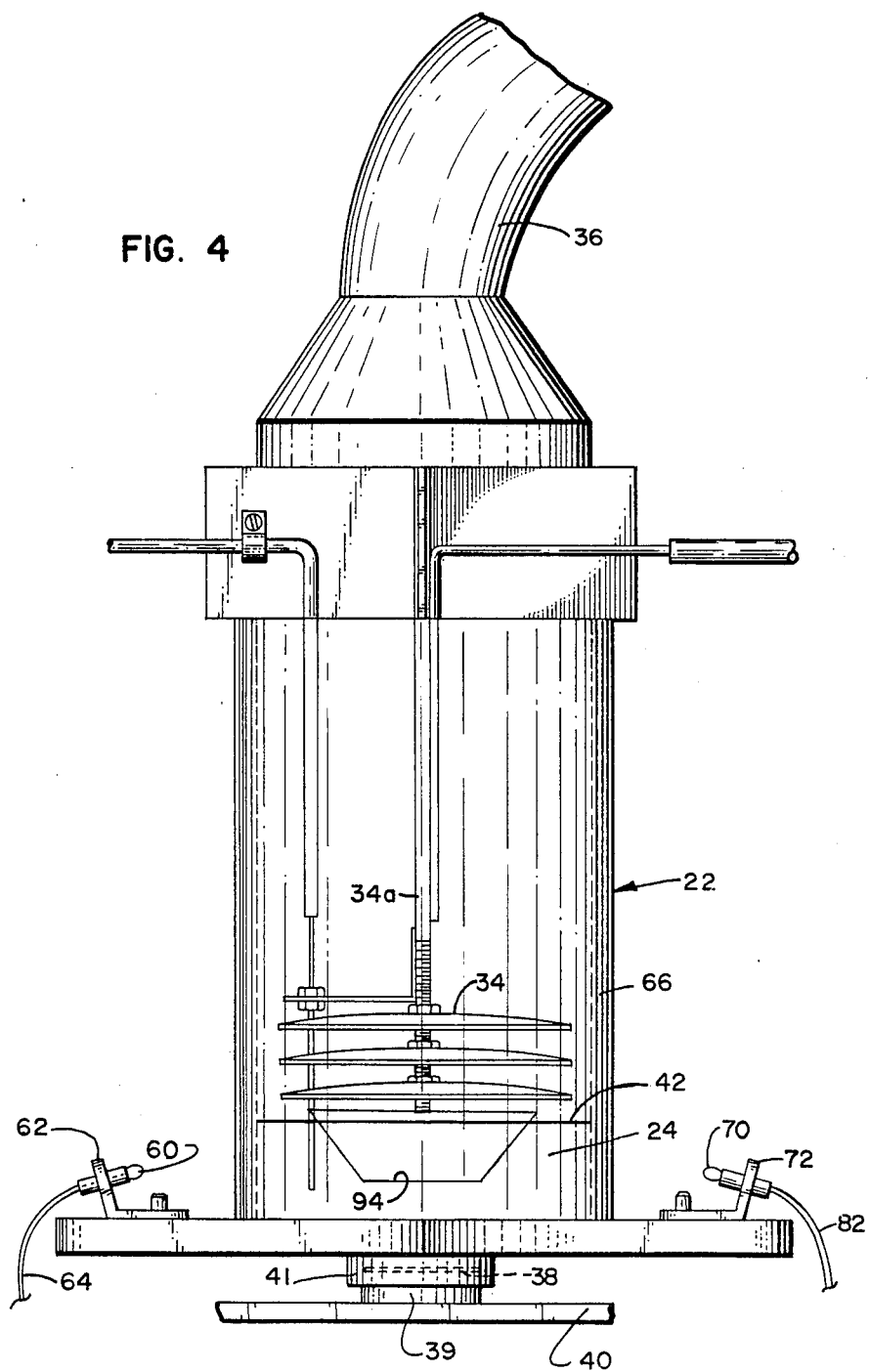
FIG. 4 is a side elevational view of an embodiment of a container arrangement in accordance with the principles of the present invention.

Referring now to the drawings, there is illustrated in FIGS. 1 through 4 a preferred embodiment of a bubble detector apparatus in accordance with the principles of the present invention, generally referred to by the reference numeral 20. As illustrated, a container 22 is provided for containing a quantity of liquid 24. In the embodiment of the invention shown, the liquid is preferably translucent, such as isopropanol. The liquid reservoir 26 and its associated valve 28 are preferably present for providing a source of liquid to the container 22 as required. In addition, a drain valve 30 is preferably present for draining the container 22. A liquid level sensor 32 is preferably present to provide an indication as to when the liquid is at a preferred height. In addition, as illustrated in FIG. 4, the container 22 might include a suitable baffle arrangement 34 and exhaust vent 36 for venting off any undesired gas fumes. Additionally, an inverted open-ended conical structure 94 is shown suitably mounted in the container 22 so as to be aligned with a longitudinal axis of the container 22. The conical structure 94 is shown interconnected to a central shaft 34a of the baffle arrangement 34, although the conical structure 94 might be supported in many different ways.

As diagrammatically illustrated in FIG. 3, filter media 38 are mounted on a fixture apparatus 40 which is pivotally mounted about an axis 37 proximate a bottom of the container 22. The fixture apparatus 40 includes a plurality of spaced apart pedestals 39 on which the filter media 38 are mounted. The filter media 38 are retained in place on the pedestals 39 by a removable cover portion 41. As illustrated in FIG. 3 by the arrows 50 the fixture apparatus 40 in the preferred embodiment is capable of holding a plurality of the filter media 38 and is rotatably mounted under the container 22 such that the filter media 38 can be individually rotated into position over an outlet 44 from a source of gas under pressure 46. Accordingly, the fixture apparatus 40 can be set up with a plurality of the filter media 38 for testing such that different filter media can be tested simply by rotating the fixture apparatus 40. It will be appreciated that numerous fixture and container arrangements might be utilized.

Figure 1:
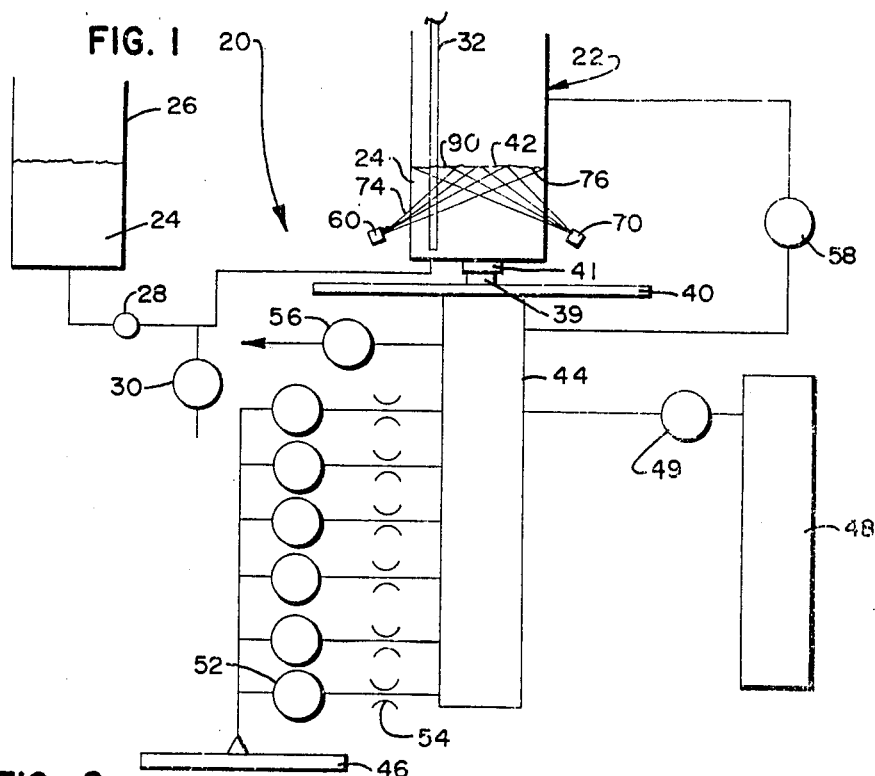
FIG. 1 is a diagrammatic view of an embodiment in accordance with the principles of the present invention.

As illustrted in FIG. 1, a gas reservoir 48 and its associated valve 49 might be provided to facilitate regulating the gas pressure, the reservoir 48 providing an enlarged volume so that pressure can be raised more slowly when a supply of gas is provided under pressure than if the reservoir were not present. A plurality of solenoid valves 52 and their associated gas flow restrictor apparatus 54 are operatively interconnected to the source of gas under pressure 46 to regulate the pressure rise in the outlet 44. In addition, a vent 56 is preferably provided for venting off the gas as required. A differential pressure sensor or transducer 58 is interconnected across the gas outlet 44 and the air in the container 22 to provide an accurate measurement of the pressure differential. As illustrated in FIGS. 1 and 4, a source of light 60 is suitably mounted by a support bracket 62 at a location below the top surface 42 of the liquid 24 so as to emit light in a direction toward the top surface 42 at an angle less than the critical angle of internal reflection of the liquid surface. The light source 60 is suitably interconnected by leads 64 to a source of energy such as an AC outlet or a DC battery. The container 22 preferably has walls 66 which are transparent along this part of the container to enable the passage of the light therethrough. Positioned on an opposite side of the container 22 at a location below the top surface 42 of the liquid 24 is a small active area photodetector apparatus 70 suitably mounted by a support bracket 72. As illustrated in FIG. 1, the photodetector apparatus 70 detects light 74 which is emitted by the light emitting source 60 and reflected off an under side 76 of the top surface 42 of the liquid 24 in a direction generally toward the photodetector apparatus 70. As illustrated in FIG. 2, in one embodiment the photodetector apparatus 70 is a one square millimeter active area phototransistor with an emitter base junction used as a photodiode 80. The photodetector apparatus 70 is electrically interconnected by leads 82 to an op-amp 84 for signal amplification, is passively high pass filtered, actively two-pole high pass filtered by a filter apparatus 86 and then passed through an adjustable threshold comparator 88 with a TTL compatable output. The amplifier and filter arrangement provides for selectively sensing a signal frequency from the photodetector apparatus 70 due to bubble produced waves 90 at the top surface 42 of the liquid 24 which create a wave pattern having an associated frequency.

In an alternative embodiment, the liquid contained in the container is preferably opaque and reflective, such as mercury. The apparatus works in essentially the same manner as does the apparatus which utilized translucent liquid. The light source 60, however, is mounted above the top surface 42 of liquid 24 at an angle below the critical angle for total external reflection of the light. The light source emits light in the direction of the top surface. Light is reflected by the top surface toward the photodetector apparatus 70, which is also mounted above the top surface of the liquid in this alternative embodiment.

Figure 5:
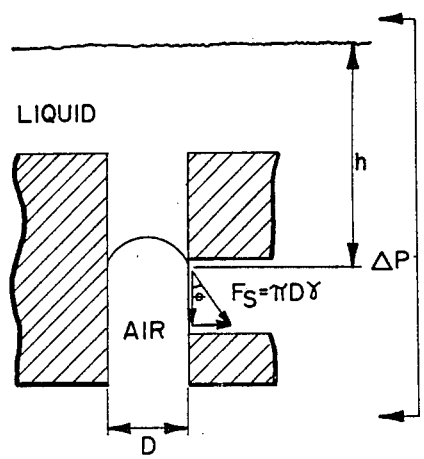
FIG. 5 is a diagrammatic view illustrating various parameters for calculation of the filter media pore diameter.

Bubbles are created when sufficient gas pressure is exerted on the side of the filter media 38 facing the gas under pressure so as to force gas through pores of the filter media 38. By knowing the pressure differential ($\Delta P$) between the gas under pressure and the normal air pressure in the container when the gas bubbles first appear, as well as certain other parameters, the maximum pore size of the filter media 38 can be determined by the following commonly known equations, with various ones of the parameters being diagrammatically illustrated in FIG. 5:

$$\Delta P = \Delta P \text{ interface} + \rho_1 g h$$

The first equation states that the pressure difference between the gas below the sample and the gas above the liquid is equal to the pressure due to the liquid column, and the pressure difference across the gas liquid interface. $\rho g h$ is the pressure due to a column of liquid of density $\rho_1$, of height h, in earth's gravity g.

$$\frac{\pi D^2}{4} \Delta P \text{ interface} - \pi D \gamma \cos\theta = 0$$

This is the force balance equation. Since the interface is stationary, the total force on the interface must be zero. The total force is made up of the upward force of the pressure difference across the interface (area × pressure, or $\pi(D/2)^2 P$ interface), and the downward force exerted by the surface tension of the liquid contact with the pore wall (circumference [$\pi D$] times the component of the force in the downward direction [$\gamma \cos\theta$]).

Combining equations 1 and 2 and solving for D $$D = \frac{4\gamma \cos\theta}{\Delta P - \rho_1 g h}$$

Wherein:

$\rho_1$ is the liquid mass density.

$\Delta P$ is the pressure difference between the gas just below the filter sample and the gas just above the liquid.

$\Delta P$ interface is the pressure difference between the gas just below the filter sample and the liquid just above the filter sample. Differs from $\Delta P$ by $\rho_1 g h$.

g is the local gravitational constant, roughly 9.8 meters per second$^2$.

$\gamma$ is the surface tension of the liquid.

$\theta$ is the wetting angle. See FIG. 5. This is the angle of the liquid contact with the pore wall. Depends on the liquid and the pore wall material.

h is the height of the liquid surface above the interface, for practical matters it is the height of the liquid surface above the filter sample.

D is the equivalent pore diameter. Filter media pores are typically not circular, and what is called the equivalent pore diameter is the diameter of a circular pore which opens at the same pressure.

Figure 6:
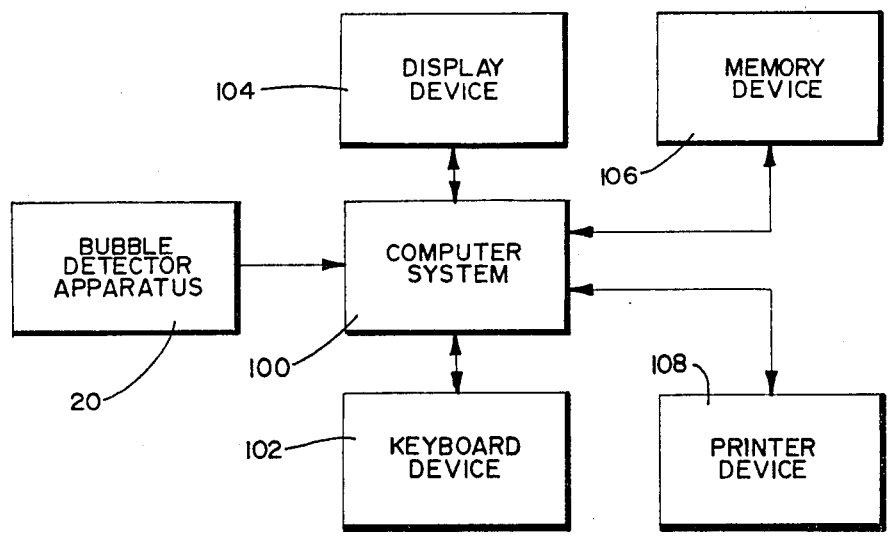
FIG. 6 is a block diagram of a computer controlled system in accordance with the principles of the present invention.

As illustrated in FIG. 6, the bubble detector apparatus 20 is preferably interconnected to a computer system 100 having an associated keyboard device 102 and display device 104, as well as memory device 106 for storage of information and printer device 108 for producing hard copy reports.

In a preferred embodiment, the six restrictor apparatus 54 are sized and calibrated to provide flows from 2.7 feet per minute to around 1200 feet per minute. By opening various combinations of the solenoid valves 52, flows from 2.7 to 1600 feet per minute are produced. An adjustable valve and a flow meter might also be used, but the restrictor method is easier to automate and interconnect to the computer system 100. The pressure across the filter media 38 varies from zero to twelve pounds per square inch. This corresponds to pore sizes from greater than one hundred microns down to around one micron. All solenoid valves 52 are preferably controlled by the computer system 100 and the pressure transducer 58 is also preferably controlled and read by the computer system.

In operation, the operator will load the filter media samples in the fixture apparatus 40. The operator will then enter via the keyboard 102 into the computer system 100 various data, including name, sample type, etc. and initiates the test. All subsequent actions from this point on are preferably computer controlled. The fixture apparatus 40 rotates the first filter media sample 38 into position over the gas outlet 44. The solenoid valves 52 are sequentially opened and the pressure drop recorded at each flow. This is done while the container 22 is dry and will provide what is known as "dry" data. Isopropanol is then added above the filter media to a depth of approximately one inch. The valve to the air reservoir is opened to slow down the rate of pressure rise below the filter media 38 and the lowest flow restrictor 54 opened. As the pressure is gradually increased, it will reach the "bubble point" when a very small stream of bubbles will appear from the largest pore of the filter media sample 38 and rise to the top surface of the liquid 24 so as to create the wave pattern. This will be detected by the photodetector apparatus 70 which will output a signal frequency representative of the wave pattern frequency which is selectively filtered and output to the computer system 100. The computer system 100 will at this time record the pressure differential across the filter media sample 38 to enable determination of the maximum pore diameter. With the isopropanol still in the container 22, the remaining solenoids 52 are sequentially opened and the pressure drop recorded at each flow. This will provide what is referred to as "wet" data. The container is then drained and various calculations performed on the raw data obtained and stored by the computer system 100. The fixture apparatus 40 is rotated to the next filter media sample 38 and "dry" data is again obtained for this particular filter media. This procedure is repeated for all of the filter media 38 in the fixture. The data obtained is then averaged and printed in a plot about the cumulative (Qwet/Qdry versus Pore diameter) and the normalized differential distribution (d(Qwet/Qdry)/dD versus pore diameter). The maximum pore size is also calculated from the pressure drop at the "bubble point" from the previously described algorithms.

It is to be understood that even though numerous characteristics and advantages of the invention has been set forth in the foregoing description, together with details of the structure and function of the invention, the disclosure is illustrative only and changes may be made in detail, especially in matters of shape, size and arrangement of parts, within the principles of the invention to the full extent indicated by the broad general meaning in which the appended claims are expressed.

What is claimed is:

1. An apparatus for determining the size of pores in a filter media, comprising:
   (a) container means for containing a liquid, the liquid having a top surface;
   (b) light emitting means for emitting light directed toward the top surface of the liquid;
   (c) disturbance means for causing bubbles of gas to rise to the top surface of the liquid from a location below the top surface of the liquid such that the top surface of the liquid is disturbed thereby causing a wave pattern at the top surface of the liquid having an associated frequency, the disturbance means including gas means for delivery of gas under pressure into the liquid of the container means at a location below the top surface of the liquid, the gas means including means for providing a path for the flow of gas into the liquid, the gas means further including means for selectively varying the gas pressure;
   (d) fixture means for mounting the filter media in the path of the gas, the filter media prohibiting the flow of the gas into the liquid over a range of gas pressures such that the wave pattern is not present, the filter media having a first side facing the liquid and a second side facing the gas under pressure;
   (e) light detecting means for detection of light emitted from the light emitting means and reflected from the top surface of the liquid, the light detecting means including output means for output of a signal indicating the presence of the wave pattern due to the gas under pressure flowing through the filter media and causing the gas bubbles to rise to the top surface of the liquid; and
   (f) frequency detection means associated with the light detecting means for receiving the signal output from the light detecting means and for detection of a predetermined signal frequency, the frequency detection means including means for output of a signal indicating detection of the predetermined signal frequency.

2. An apparatus for determining the size of pores in a filter media, comprising:
   (a) container means for containing a liquid, the liquid having a top surface;
   (b) light emitting means for emitting light directed toward the top surface of the liquid;
   (c) disturbance means for causing bubbles of gas to rise to the top surface of the liquid from a location below the top surface of the liquid such that the top surface of the liquid is disturbed thereby causing a wave pattern at the top surface of the liquid having an associated frequency, the disturbance means including gas means for delivery of gas under pressure into the liquid of the container means at a location below the top surface of the liquid, the gas means including means for providing a path for the flow of gas into the liquid, the gas means further including means for selectively varying the gas pressure;
   (d) fixture means for mounting the filter media in the path of the gas, the filter media prohibiting the flow of the gas into the liquid over a range of gas pressures such that the wave pattern is not present, the filter media having a first side facing the liquid and a second side facing the gas under pressure;
   (e) light detecting means for detection of light emitted from the light emitting means and reflected from the top surface of the liquid, the light detecting means including output means for output of a signal indicating the presence of the wave pattern due to the gas under pressure flowing through the filter media and causing the gas bubbles to rise to the top surface of the liquid, the signal output having a frequency representative of the frequency of the wave pattern; and
   (f) means for determining the frequency of the signal output from the light detecting means.

3. An apparatus in accordance with claim 1, wherein the frequency detection means includes filter means for filtering out all frequencies other than the predetermined frequency.

4. An apparatus for detecting the size of the pores in a porous filter media, comprising:
   (a) reservoir means for containing a liquid, the liquid having a top surface with a top side and an under side;
   (b) light emitting means for emitting light directed toward the top surface of the liquid;
   (c) a source of gas under pressure, including an outlet means for providing gas under pressure to the liquid in the reservoir;
   (d) fixture means for retaining a filter media in association with the reservoir means so as to obstruct the output means with the filter media, a side of the filter media facing the liquid and a side of the filter media facing the gas under pressure;
   (e) means associated with the gas under pressure for selectively varying the pressure applied against the side of the filter media by the gas, whereby at some range of gas pressure bubbles are formed on the liquid side of the filter media and rise to the top surface of the liquid thereby creating a wave disturbance resulting in a wave pattern at the top surface of the liquid having an associated frequency;

(f) light detecting means for detecting variations in the amount of light emitted from the light emitting means and subsequently reflected from the top surface of the liquid, the light detecting means including means for output of a signal having a frequency representative of the frequency of the wave pattern;

(g) filter means operatively interconnected to the detecting means for filtering out all but a predetermined frequency, the filter means including means for transmitting a signal indicating detectiion of the predetermined frequency;

(h) pressure differential means for sensing the pressure differential between the gas under pressure and the gas pressure in the container above the top surface of the liquid; and (i) means operatively interconnected to the filter means for receiving the signal output by the filter means and operatively interconnected to the pressure differential means for receiving a signal from the pressure differential indicative of the pressure differential.

5. An apparatus in accordance with claim 4, wherein the means operatively interconnected to the filter means and the pressure differential means includes computer means for storing information represented by the signals received from the filter means and the pressure differential means and for performing analysis on the information.

6. A method for determining the porosity of a porous filter media, comprising:

(a) positioning a filter media in association with a reservoir containing liquid such that the filter media is positioned over an outlet from a source of gas under pressure, one side of the filter media facing the liquid and one side facing the gas under pressure;

(b) selectively varying the amount of pressure exerted by the gas against the filter across a range of gas pressures such that at one end of the range of gas pressure bubbles are formed on a liquid side of the filter media, thereby causing a wave pattern at the top surface of the liquid having an associated frequency;

(c) directing a light source toward the top surface of the liquid;

(d) detecting the amount of light reflected from the top surface of the liquid; and (e) detecting the presence of the wave pattern by by detecting the variation in light reflected from the top surface of the liquid.

7. A method in accordance with claim 6 wherein the step of determining the amount of light reflected includes the step of outputting a signal representative of the frequency of the wave pattern, amplifying the signal and selectively filtering out all but a predetermined frequency, and output of a second signal indicative of the presence of the predetermined wave pattern frequency.

8. A method in accordance with claim 7 including monitoring the second signal and the amount of pressure exerted against the filter media and recording the gas pressure differential between the pressure exerted by the gas under pressure and the air in the reservoir above the top surface of the liquid when the wave pattern is initially detected.

* * * * *

UNITED STATES PATENT AND TRADEMARK OFFICE
CERTIFICATE OF CORRECTION

PATENT NO.  : 4,779,448

DATED       : October 25, 1988

INVENTOR(S) : Mark A. Gogins

It is certified that error appears in the above-identified patent and that said Letters Patent is hereby corrected as shown below:

Page 1, Abstract, Line 1, "buffle" should be --bubble--.
Col. 1, Line 25, "abovedescribed" should be --above-described--.
Col. 2, Line 4, "bubbles" should be --bubble--.
Col. 3, Line 11, "is" should be --in--.
Col. 3, Lines 31-32, after "are" delete "features of novelty which characterize the invention are".
Col. 3, Line 33, "particularly" should be --particularity--.
Coo. 3, Line 34, "thereof" should be --hereof--.
Col. 4, Line 41, "illustrted" should be --illustrated--.
Col. 5, Line 15, "compatable" should be --compatible--.
Col. 5, Line 24, "utilized" should be --utilizes--.
Col. 5, Line 52, "gasliquid" should be --gas-liquid--.
Col. 7, Line 24, "has" should be --have--.
Col. 7, Line 25, "foreging" should be --foregoing--.
Col. 10, Line 16, delete second occurrence of "by".

Signed and Sealed this

Twenty-eighth Day of March, 1989

Attest:

DONALD J. QUIGG

Attesting Officer

Commissioner of Patents and Trademarks